United States Patent [19]

Moore

[11] Patent Number: 4,550,866
[45] Date of Patent: Nov. 5, 1985

[54] OCULAR DISPENSER

[76] Inventor: Lawrence F. Moore, 501 Lake Shore Dr., Lake Park, Fla. 33403

[21] Appl. No.: 529,395

[22] Filed: Sep. 6, 1983

[51] Int. Cl.[4] .............................................. B05B 11/04
[52] U.S. Cl. .................................... 222/420; 604/294
[58] Field of Search ............................. 604/294—302; 222/215, 420; D22/15; 273/408, 409

[56] References Cited

U.S. PATENT DOCUMENTS 3,979,117  9/1976  Worsham ............................. 273/408
4,257,417  3/1981  Gibilisco ............................. 604/302
4,408,699  10/1983  Stock ............................. 222/420 X

FOREIGN PATENT DOCUMENTS 2053840  6/1980  United Kingdom ................. 604/294

Primary Examiner—Stanley H. Tollberg
Attorney, Agent, or Firm—James E. Brunton

[57] ABSTRACT

An ocular dispensing device for use with fluid eye medicine containers which is characterized by having an upstanding nozzle portion being of at least a first color different from the color of the container and a background flange portion being of at least a second color different from the color of the container. The multicolored aspect of the device creates a target-like effect which permits the patient to accurately focus upon the nozzle and to precisely position it relative to the eye when the medicine is being dispensed into the eye.

4 Claims, 6 Drawing Figures

OCULAR DISPENSER

BACKGROUND OF THE INVENTION

1. Field of the Invention

The present invention relates generally to devices for dispensing and applying medications to the eye. More particularly, the invention concerns a uniquely configured, multicolor device which is attachable to a fluid medicine container for dispensing fluid therefrom into the eye.

2. Discussion of the Prior Art

In the past eye droppers and eye cups were commonly used for dispensing liquid medicines and eye washes into the eyes. More recently, however, manufacturers of eye medicines have developed plastic fluid medicine containers which embody an integral nozzle-like element through which the medicine is dispensed. Typically, the plastic containers have yieldably deformable, thin wall body portions which can be squeezed to force the medicine through a small fluid passageway formed in the nozzle. As a general rule, the plastic materials used in forming the container and the nozzle are opaque or of a single color, usually white.

Substantial difficulty and risk is experienced by a person using either an eye dropper or the newer plastic dispensing devices. In the first place the user has difficulty in keeping the eye to be treated open with the head thrown back and at the same time focusing on the device so that it can be positioned accurately for treatment. Improper positioning of the device relative to the eye results in little, if any, of the medicine getting into the eye so that several attempts at treatment are usually required. This is time consuming and often substantial amounts of the costly medicine is wasted. Secondly, and of critical importance, is the fact that because of the difficulty in seeing the device, particularly after some of the medication reaches the eye, there is a substantial danger of injury if the nozzle or eye dropper accidentally engages the eye ball.

The fact that the nozzle, and usually the fluid container, are either opaque or are of a single color, contributes to the patient' difficulty in focusing on the nozzle portion of the device because it is seen by the eye as a shape having no lines of delineation. Additionally, the reflex action of the person when the medicine impacts upon the eye ball further contributes to the risk of serious injury if the nozzle is not properly spaced from the eye.

SUMMARY OF THE INVENTION

This invention has for its primary object the provision of a novel multicolored, uniquely configured ocular dispenser adapted for use with the commercially available, white or opaque plastic eye medicine containers. The dispenser is constructed of plastic, or other suitable material, and includes an upstanding nozzle portion of at least a first color and a flange portion of at least a second color. With this arrangement, the nozzle portion becomes clearly visible by color contrast with the background flange portion and container and the user can readily focus on the nozzle and accurately judge its position relative to the eye.

Another object of the invention is to provide a device of the aforementioned character in which the flange portion is provided with upstanding ridges of a third color which act as a "cross-hair" like target to enhance focusing upon the nozzle and also enable precise centering of the nozzle relative to the eye.

Still another object of the invention is to provide a device as described in the preceding paragraphs which can readily be substituted for the opaque, or white, nozzle typically provided with commercially available plastic eye drop dispensing containers.

Yet another object of the invention is to provide a dispenser of the class described which is simple and safe to use and one which can be inexpensively manufactured in large quantities.

These and other objects of the invention will become apparent from the description which follows.

DESCRIPTION OF THE INVENTION

Figure 1:
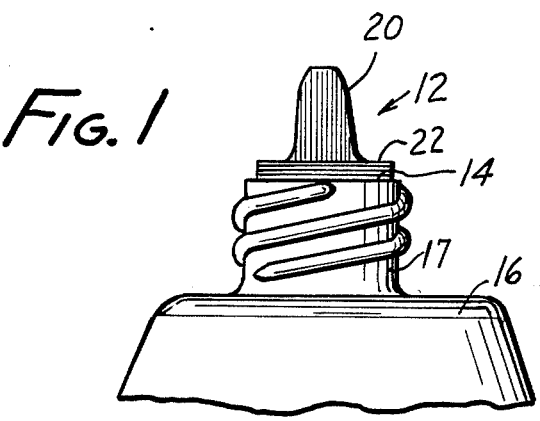
FIG. 1 is a fragmentary side elevational view of one form the ocular dispenser of the invention in position within an open top container adapted to contain medication.
Figure 2:
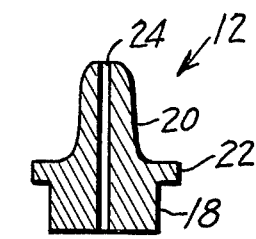
FIG. 2 is a side elevation, cross-sectional view of the ocular dispenser of this form of the invention.
Figure 3:
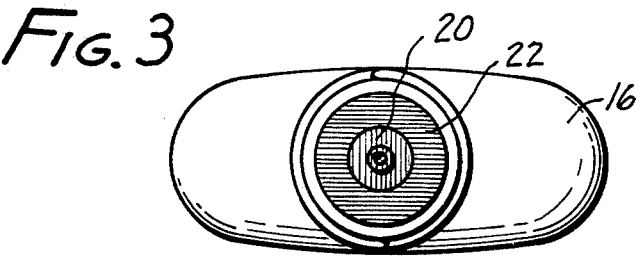
FIG. 3 is a plan view of the combination ocular dispenser and medication container illustrated in FIG. 1.

Referring to the drawings, and particularly to FIGS. 1 through 3, the ocular dispenser 12 of one form of the present invention is adapted to be inserted in the open upper end 14 of a container 16 containing medication, such as eye drop fluid. As best seen in FIG. 2, dispenser 12 comprises a lower generally cylindrically shaped portion 18 adapted to be closely telescopically received within the open top 14 of the container 16. Integrally formed with portion 18 is an upper nozzle portion 20 which is of a first color different from the color of the container 16. Formed intermediate lower portion 18 and nozzle portion 20 is an intermediate flange portion 22, at least a portion of which is a third color different from the color of the container 16.

As previously mentioned, container 16, which is typically formed of a plastic material, has thin, side wall body portions which can be deformed inwardly to force the eye drop fluid or other medicine through a small fluid passageway 24 (FIG. 2) formed in the dispensing device 12. The neck 17 of the container is externally threaded to receive a closure cap (not shown).

As a general rule, the plastic material used in forming the container 16 is opaque, or sometimes white in color. Assuming this to be the case, and by way of example, the nozzle portion 20 of the dispensing device can be colored red, while the flange portion 22 thereof can be colored blue. As best seen in FIG. 3, with this arrangement, the user of the device will see a red nozzle 20 against against a blue background of the flange 22 which in turn appears against the white background of the container 16. Accordingly, when the bottle, is inverted into a fluid dispensing position it appears to have defined thereon a "target" area, the center of which is the red nozzle, the surrounding area of which is the blue flange 22 and the general background thereof is the white or opaque plastic container 16. This "target" area enables the user to clearly focus his eye upon the red nozzle 20 appearing against the blue background 22 to quickly and and accurately center the nozzle and precisely position it in an optimum spaced apart position from the eye. This avoids waste of the costly medicine and provides a real safeguard against an accidental touching of the eyeball by the nozzle portion 20.

It is to be understood that the colors described are exemplary only and various colors can be used to distinguish the nozzle from the flange. The colors can be impregnated into the material from which the dispensing device is formed or they can be applied to the surfaces thereof in ways well known to those skilled in the art.

In actual practice, the ocular dispenser portion 12 is preferably formed of a moldable plastic and is configured so as to readily fit within the opening 14 of most commercially available plastic bottles or containers containing eye drops, eye wash, or other ocular medication. By simply removing the nozzle assembly provided by the manufacturer and replacing it with the ocular dispenser of the present invention, the otherwise dangerous dispenser can be converted into a safe, easy to use device for unassisted dispensing of the fluid into the eye by the patient.

Figure 4:
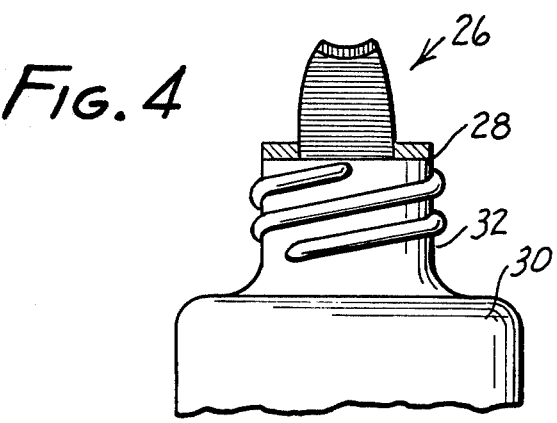
FIG. 4 is a fragmentary side elevational view of an alternate form of ocular dispenser of the invention interconnected with a container of different configuration.
Figure 5:
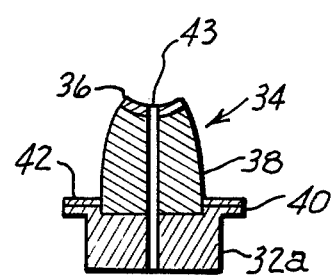
FIG. 5 is a side elevation, cross-sectional view of the ocular dispenser of this second form of the invention.
Figure 6:
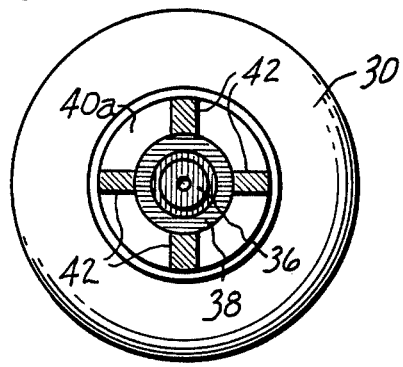
FIG. 6 is a plan view of the combination ocular dispenser and medicine container illustrated in FIG. 4.

Turning now to FIGS. 4, 5 and 6, there is shown another form of the ocular dispenser of the present invention. In this form of the invention, the dispensing device 26 is once again adapted to be closely received within the open top 28 of a second form of medicine container 30. As best seen in FIG. 6, this second type of squeeze bottle is generally circular in cross-section at any point and has at its upper end an open externally threaded neck portion 32. Once again, container 30 is typically constructed of a plastic material, usually opaque, or white in color.

Referring to FIG. 5, the device of this form of the invention includes a lower portion 32a adapted to be partially received within the opening 28 of container 30 and an upper nozzle portion 34. The nozzle portion 34 is generally circular in cross-section at any point and comprises a first upper portion 36 and a second lower portion 38. Formed intermediate of portions 32a and 38 is a flange portion 40 having a plurality of radially outwardly extending ridges 42 protruding upwardly from an upper generally planar surface 40a (FIG. 6) of flange 40. As best seen by referring to FIG. 6, the flanges 42 of the form of the invention shown in the drawings are circumferentially spaced apart by approximately 90°. With this arrangement, a "cross-hair" like effectis created. As best seen in FIG. 5, the device is provided with an axially extending fluid passageway 43 which is adapted to communicate with the interior of the container 30 when the device is connected to the container.

To once again make maximum use of the advantages of color differentiation as an aid in focusing upon the nozzle, the upper portion 36 of the nozzle is formed of a first color, while the lower portion 38 is formed of a second color. Similarly, the planar portion 40a of flange 40 is preferably formed of a third color while the upstanding ridge portions 42 are formed of a fourth color. This arrangement gives a vivid color pattern to the viewer, which, as best seen in FIG. 6, appears to be a cross, or "cross-hair" like configuration having a multicolored target-like area superimposed thereover. By way of example, upper portion 36 of the nozzle may be colored red, lower portion 38 of the nozzle may be colored blue, the planar surface 40a of the flange may be colored yellow and the upstanding flange portions 42 may be colored green. It is apparent that such a vivid color pattern in the unique configuration illustrated in FIG. 6 provides a unique mechanism for easy focusing and centering of the nozzle portion of the device relative to the eyeball. Once again it is to be noted that various colors can be used to create the desired color differentiation effect.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. In combination with a container containing medicine, a closure therefor comprising a body having a fluid passageway therethrough in communication with the interior of the container, said body including:
   (a) a lower portion adapted to be partially received with said container;
   (b) a nozzle portion being generally circular in cross-section at any point and comprising a first upper portion of a first color different from the color of the container and a second lower portion of a second color different from the color of the container; and
   (c) an intermediate flange portion having a planar surface of a third color and a plurality of radially outwardly extending ridges protruding upwardly from said planar surface, said ridges being of a fourth color.

2. A closure as defined in claim 1 in which said ridges are circumferentially spaced apart by 90 degrees.

3. The combination as defined inclaim 2 in which said nozzle portion is red.

4. The combination as defined in claim 3 in which said flange portion is white and said ridges are blue.

* * * * *